US008404263B2

(12) United States Patent
Ishaque et al.

(10) Patent No.: US 8,404,263 B2
(45) Date of Patent: Mar. 26, 2013

(54) AGROCHEMICAL FORMULATIONS COMPRISING A PESTICIDE, AN ORGANIC UV-PHOTOPROTECTIVE FILTER AND COATED METAL-OXIDE NANOPARTICLES

(75) Inventors: Michael Ishaque, Mannheim (DE); Gerhard Schnabel, Elsenfeld (DE); Douglas D. Anspaugh, Apex, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/999,912

(22) PCT Filed: Jun. 15, 2009

(86) PCT No.: PCT/EP2009/057329
§ 371 (c)(1),
(2), (4) Date: Dec. 17, 2010

(87) PCT Pub. No.: WO2009/153231
PCT Pub. Date: Dec. 23, 2009

(65) Prior Publication Data
US 2011/0111957 A1  May 12, 2011

(30) Foreign Application Priority Data

Jun. 20, 2008 (EP) .................... 08158664

(51) Int. Cl.
*A01N 25/00* (2006.01)
*A01N 59/16* (2006.01)
*A61K 33/08* (2006.01)
(52) U.S. Cl. ......... 424/405; 424/641; 424/688; 504/121
(58) Field of Classification Search .................. None
See application file for complete search history.

(56) References Cited

U.S. PATENT DOCUMENTS

| | | | |
|---|---|---|---|
| 4,171,355 A | 10/1979 | Stubbs et al. | |
| 4,259,189 A | 3/1981 | Li | |
| 4,926,190 A | 5/1990 | Laver | |
| 4,973,702 A | 11/1990 | Rody et al. | |
| 6,395,776 B1 | 5/2002 | Loesel et al. | |
| 2004/0062728 A1 | 4/2004 | Boutelet et al. | |
| 2006/0041038 A1 | 2/2006 | Xia | |
| 2006/0194057 A1 | 8/2006 | Pfluecker et al. | |
| 2011/0237665 A1 | 9/2011 | Misske et al. | |
| 2011/0257265 A1 | 10/2011 | Ishaque et al. | |

FOREIGN PATENT DOCUMENTS

| | | |
|---|---|---|
| CA | 2 006 418 | 6/1990 |
| CA | 2 091 064 | 3/1992 |
| DE | 19 14 059 | 10/1970 |
| DE | 195 28 529 | 2/1997 |
| DE | 10333029 | 2/2005 |
| EP | 0 057 160 | 6/1985 |
| EP | 0 280 650 | 8/1988 |
| EP | 0 376 888 | 7/1990 |
| EP | 496106 | * 7/1992 |
| EP | 0 513 902 | 11/1992 |
| EP | 0496106 | 12/1995 |
| EP | 0 845 942 | 10/2002 |
| EP | 1 401 832 | 2/2005 |
| JP | 4 198 148 | 7/1992 |
| WO | WO 92/03926 | 3/1992 |
| WO | WO 96/33611 | * 10/1996 |
| WO | WO 97/42815 | 11/1997 |
| WO | WO 03/063814 | 8/2003 |
| WO | WO 03063814 | * 8/2003 |
| WO | WO 2004/052327 | 6/2004 |
| WO | WO 2005/015993 | 2/2005 |
| WO | WO 2005/072680 | 8/2005 |
| WO | WO-2005072680 | * 8/2005 |
| WO | WO 2006/077394 | 7/2006 |
| WO | WO 2006/089747 | 8/2006 |
| WO | WO 2008/085682 | 7/2008 |
| WO | WO 2009/153231 | 12/2009 |
| WO | WO 2010/063657 | 6/2010 |
| WO | WO 2010/103021 | 9/2010 |

OTHER PUBLICATIONS

Kuehr et al., *Titanium dioxide photoinduced degradation of some pesticide/fungicide precursors*, Pest Management Science, 2007, vol. 63, pp. 491-494.

Miskus et al., *Stabilization of thin films of pyrethrins and allethrin*, Journal of Agricultural and Food Chemistry, 1972, vol. 20, pp. 313-315.

Topalov et al., *Photocatalytic Oxidation of the Fungicide Metalaxyl Dissolved in Water over TiO₂*, Water Research, 1999, vol. 33, pp. 1371-1376.

BASF, "Uvinul grades. UV absorbers for cosmetic products", Technical Information BASF, Aug. 1995, pp. 1-21.

Hu, Ji Ye et al., "Photodegradation of Flumorph in Aqueous Solutions and Natural Water under Abiotic Conditions", J. Agric. Food Chem., 2009, pp. 9629-9633, vol. 57, No. 20.

Hussain, M., et al., "The Effect of Selected UV Absorber Compounds on the Photodegradation of Pyrethroid Insecticides Applied to Cotton Fabric Screens", Pesticide Science, (1990), pp. 345-355, vol. 28.

(Continued)

*Primary Examiner* — Alton Pryor
(74) *Attorney, Agent, or Firm* — Brinks Hofer Gilson & Lione

(57) ABSTRACT

The resent invention relates to an agrochemical formulation comprising a pesticide, an organic UV photoprotective filter and coated metal oxide nanoparticles. It also relates to a method for preparing said formulation. Further on, it also relates to the use of a mixture of an organic UV photoprotective filter and coated metal oxide nanoparticles in agrochemical formulations and the use of a agrochemical formulation according to the invention for stabilizing a pesticide against UV irradiation. Further on, it relates to a method of combating harmful insects and/or phytopathogenic fungi, which comprises contacting plants, soil or habitat of plants in or on which the harmful insects and/or phytopathogenic fungi are growing or may grow, plants or soil to be protected from attack or infestation by said harmful insects and/or phytopathogenic fungi with an effective amount of the formulation according to the invention, to a method of controlling undesired vegetation, which comprises allowing a herbicidal effective amount of said formulation to act on plants, their habitat.

12 Claims, No Drawings

OTHER PUBLICATIONS

Philippon, A. et al., "Macrocyclic Ethers by Free Radical Cyclizations", Synthetic Communications, (1997), pp. 2651-2682, vol. 27.

Takagi, K. et al., "Discovery of metaflumizone, a novel semicarbazone insecticide", Veterinary Parasitology, 2007, pp. 177-181, vol. 150.

Waldeck, D.H., "Photoisomerization Dynamics of Stilbenes", Chem. Rev. 1991, pp. 415-436, vol. 91.

Wyman, G.M., "The *Cis-Trans* Isomerization of Conjugated Compounds", Chem. Rev. 1955, pp. 625-657.

* cited by examiner

AGROCHEMICAL FORMULATIONS COMPRISING A PESTICIDE, AN ORGANIC UV-PHOTOPROTECTIVE FILTER AND COATED METAL-OXIDE NANOPARTICLES

This application is a National Stage application of International Application No. PCT/EP2009/057329 filed Jun. 15, 2009, the entire contents of which is hereby incorporated herein by reference. This application also claims priority under 35 U.S.C. §119 to European Patent Application No. 08158664.6, filed Jun. 20, 2008, the entire contents of which is hereby incorporated herein by reference.

The resent invention relates to an agrochemical formulation comprising a pesticide, an organic UV photoprotective filter and coated metal oxide nanoparticles. It also relates to a method for preparing said formulation. Further on, the present invention relates to a kit of parts, comprising as separate components A) an agrochemical formulation comprising a UV photoprotective filter and a coated, nanoparticular metal oxide, and B) a pesticide for combined application in a method of combating undesired vegetation, harmful insects and/or phytopathogenic fungi. It also relates to the use of a mixture of an organic UV photoprotective filter and coated metal oxide nanoparticles in agrochemical formulations and the use of a agrochemical formulation according to the invention for stabilizing a pesticide against UV irradiation. Further on, it relates to a method of combating harmful insects and/or phytopathogenic fungi, which comprises contacting plants, soil or habitat of plants in or on which the harmful insects and/or phytopathogenic fungi are growing or may grow, plants or soil to be protected from attack or infestation by said harmful insects and/or phytopathogenic fungi with an effective amount of the formulation according to the invention, to a method of controlling undesired vegetation, which comprises allowing a herbicidal effective amount of said formulation to act on plants or their habitat. Combinations of preferred embodiments with other preferred embodiments are within the scope of the present invention.

Many pesticides are sensitive to sunlight and decompose. The decomposition might already take place already during storage or even more after application to the environment. As a result, the pesticidal activity decreases, higher amounts of pesticides have to be applied, the pesticides have to be applied in shorter intervals, or eventually toxic degradation products are produced.

Agrochemical formulations comprising a pesticide and an organic UV photoprotective filter are known: Miskus et al., J. Agr. Food Chem. 1972, 20, 313-315 disclose a combination of an UV absorber and an antioxidant in mineral oil formulation for stabilizing parethroid insecticides. EP 0 496 106 B1 discloses agrochemical formulations comprising an unsaturated amine derivative, a solid carrier and optionally UV absorbents. Further on, UV scattering agents such as titanium dioxide are optionally employed in the composition. EP 1 719 409 A1 discloses an insecticide composition comprising optionally UV absorber or UV scattering agents e.g. titanium dioxide. WO2006/077394 discloses the use of a dye for the protection of an active component contained within a microcapsule from UV degradation.

The use of titanium dioxide in the agrochemistry is known: WO 2007/014826 discloses the use of a preparation containing a UV radiation absorbing metal oxide powder and a superspreading agent for the reduction of sunburn damage to useful plants. EP 1 139 763 B1 discloses the use of a particulate material such as titanium dioxide to reduce physiological disorders of a plant without diminishing photosynthesis. WO 2005/072680 discloses a particle of TiO2 or ZnO, which has been doped with one or more other elements such that the concentration of dopant in a surface of the particle is greater than that at a core of the particle.

Although a positive effect of titanium dioxide on plants was described, a severe disadvantage of titanium dioxide is known: Topalov et al., Water Research 1999, 33, 1371-1376 disclose the photocatalytic activity of titanium dioxide towards the decomposition of the fungicide metalaxyl. Kuer and Nunez, Pest Management Science, 2007, 63, 491-494, disclose the degradation of nitrogen heterocycles, the basic structural units of a large number of commercial herbicides and fungicides, using titanium dioxide as photocatalyst. In the abstract of JP2004323501 titanium dioxide is disclosed as photocatalyst for decomposing residual agrochemicals used for the agricultural products.

The object of the invention was to provide an agrochemical formulation comprising a pesticide, which reduces the decomposition of the pesticide due to sunlight, especially due to ultraviolet (UV) light. Another object was to increase the stability of agrochemical formulation of pesticides during storage and/or after application to the environment. Yet another object was to increase the pesticidal activity of agrochemical formulations after application to the environment.

The objects were achieved by an agrochemical formulation comprising a pesticide, an organic UV photoprotective filter and coated metal oxide nanoparticles.

The mean particle size of the coated metal oxide nanoparticles is in the range from 1 to 1000 nm, preferably 1 to 100, more preferably 10 to 20 nm, determined by means of X-ray diffraction spectroscopy.

The term "coated metal oxide nanoparticles" relates to one type or a mixture of different types of said compounds. Suitable metal oxides are for example titanium oxide (amorphous or crystallized in rutile and/or anatase form), iron oxide, zinc oxide, zirconium oxide or cerium oxide. For the purposes of the present invention, preferred metal oxides to be mentioned are titanium dioxide and zinc oxide, particularly preferably titanium dioxide.

The term "coated" or "coating" means, that the metal oxide nanoparticles have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminum salts of fatty acids, metal (e.g. titanium or aluminum) alkoxides, polyethylene, silicones, proteins (collagen or elastin), alkanolamines, silicon oxides, metal oxides, sodium hexametaphosphate, alumina or glycerol. Such a surface treatment results in a coating of the metal oxide nanoparticle.

In a preferred embodiment, the coating of the metal oxide nanoparticles comprises a silicon containing polymer and/or an inorganic oxide. More preferably, the coating comprises a silicon containing polymer, or a silicon containing polymer and an inorganic oxide. Especially preferred is a coating, which comprises a silicon containing polymer and an inorganic oxide.

The term "silicon containing polymer" refers to synthetic polymeric compounds comprising silicon atoms, which are linked via oxygen atoms to polymers and wherein the residual valences of the silicon atoms are saturated by hydrogen and/or organic residues. Examples of silicon containing polymers are silicones, such as methicone or a copolymer of methicone and dimethicone.

The term "inorganic oxide" refers to oxides and hydroxides of inorganic elements, such as of silicon (e.g. silica $SiO_2$), aluminum (e.g. alumina $Al_2O_3$, or aluminum hydroxide Al(OH)$_3$), zirconium or iron, preferably aluminum and silicon. Preferred inorganic oxides are alumina, aluminum hydroxide and silica.

In one embodiment, the coating of the metal oxide nanoparticles comprises a silicon containing polymer and an inorganic oxide. Suitable examples include, but are not limited to coated titanium oxide nanoparticles, which were surface-treated with silica, alumina and silicone (such as the products "Microtitanium Dioxide MT 100 SAS", "Microtitanium Dioxide MT 600 SAS" and "Microtitanium Dioxide MT 500 SAS" from the company Tayca) or alumina and silicone (such as the product "UVT-M262" from the company Kemira). Further examples of coated titanium dioxide nanoparticles are available from BASF SE as T-Lite SF (titanium dioxide coated with aluminum hydroxide and dimethicone/methicone copolymer; titanium dioxide content 79-89 wt %), T-Lite SF-S (titanium dioxide coated with hydrated silica, dimethicone/methicone copolymer and aluminum hydroxide; titanium dioxide content 73-83 wt %) or T-lite MAX (titanium dioxide coated with dimethoxydiphenylsilane/triethoxycaprylylsilane crosspolymer, hydrated silica and aluminum hydroxide; titanium dioxide content 69-73 wt %). Each of the aforementioned T-Lite products has a crystallite size of 14-16 nm, an average particle length of 50 nm and width of 10 nm. Further examples of coated zinc oxide nanoparticles are those sold under the name "Daitopersion ZN-30" and "Daitopersion ZN-50" by the company Daito (dispersions in cyclopolymethylsiloxane/oxyethylenated polydimethylsiloxane, containing 30% or 50% of nanozinc oxides coated with silica and polymethylhydrogenosiloxane), or those sold under the name "Fuji ZNO-SMS-10" by the company Fuji Pigment (ZnO coated with silica and polymethylsilsesquioxane).

In another embodiment, the coating of the metal oxide nanoparticles comprises a silicon containing polymer. The coating may comprise at least one silicon containing polymer. Preferably, it comprises one of said polymers. Suitable examples include, but are not limited to titanium oxides nanoparticles treated with octyltrimethylsilane (such as "T 805" by the company Degussa), with a polydimethylsiloxane (such as the product sold under the trade name "70250 Cardre UF TiO2SI3" by the company Cardre), with a polydimethylhydrogenosiloxane (such as the product sold under the trade name "Microtitanium Dioxide USP Grade Hydrophobic" by the company Color Techniques). Further examples are those of coated zinc oxide nanoparticles, which are sold under the name "Zinc Oxide CS-5" by the company Toshibi (ZnO coated with polymethylhydrogenosiloxane), "SPD-ZI" by the company Shin-Etsu (ZnO coated with silicone-grafted acrylic polymer, dispersed in cyclodimethylsiloxane). Further coated zinc oxide particles are commercially available from BASF SE as Z-COTE HP1 (98 wt % zinc oxide and 2 wt % triethoxycaprylylsilane) or Z-COTE MAX (96-99 wt % zinc oxide and 1-4 wt % dimethoxydiphenylsilane/triethoxycaprylylsilane crosspolymer).

In another embodiment, the coating of the metal oxide nanoparticles comprises an inorganic oxide. The coating may comprise at least one inorganic oxide. Preferably, it comprises one inorganic oxide. Suitable examples include, but are not limited to titanium oxide nanoparticles, which were surface-treated silica and alumina (such as the products "Microtitanium Dioxide MT 500 SA" and "Microtitanium dioxide MT 100 SA" from the company Tayca, and the products "Tioveil Fin", "Tioveil OP", "Tioveil MOTG" and "Tioveil IPM" from the company Tioxide), alumina and aluminum stearate (such as the product "Microtitanium Dioxide MT 100 T" from the company Tayca), alumina and aluminum laurate (such as the product "Microtitanium Dioxide MT 100 S" from the company Tayca), iron oxides and iron stearate (such as the product "Microtitanium Dioxide MT 100 F" from the company Tayca), alumina and stearic acid (such as the product "UVT-M160" from the company Kemira), alumina and glycerol (such as the product "UVT-M212" from the company Kemira).

The metal oxide nanoparticles may have undergone one or at least two surface treatments. Preferably, the nanoparticles have undergone at least two surface treatments. Thus, the nanoparticles may have a single or more coatings (muilticoating). Preferably, the nanoparticle has a multicoating. The coating may be a multicoating of an inorganic oxide, preferably aluminum oxide, and a silicon containing polymer, preferably methicone or a copolymer of methicone and dimethicone (CAS No: 68037-59-2). Preferably, the coating comprises silicon dioxide as additional component. The designation methicone and dimethicone stands for methyl hydrogen polysiloxane and dimethyl polysiloxane, respectively.

Particularly preferred coated metal oxide nanoparticles are those in which the particles are coated by a first layer of metal oxide, preferably aluminum oxide or a mixture of aluminum oxide and silicon dioxide and an outer layer of a silicon containing polymer, preferably a copolymer of methicone and dimethicone.

The coated metal oxide particles used according to the present invention are obtainable, for example, as described in U.S. Pat. No. 6,660,380 for coated zinc oxide particles, in DE 36 42 794 A1, in EP 0 603 627 A1 or in WO 1997/16156.

In general, the coated metal oxide nanoparticles have a metal oxide content of 50 to 99.9% by weight, preferably 60 to 99.9% and most preferably 70 to 99.5% by weight. In a further preferred embodiment the coated titanium dioxide particles have a titanium dioxide content of from 70 to 92% by weight, preferably 72 to 90% by weight, particularly preferably 73 to 83% by weight. In a further preferred embodiment the coated zinc dioxide particles have a zinc dioxide content of from 70 to 99.9% by weight, preferably 90 to 99.9% by weight, particularly preferably 95 to 99.5% by weight. The percentages by weight refer to the total weight of the corresponding coated metal oxide nanoparticles.

In general, the coated metal oxide nanoparticles have a silicon containing polymer content of 0.1 to 20% by weight, preferably 0.3 to 15% and most preferably 0.5 to 10% by weight. Usually, the coated titanium dioxide nanoparticles have a silicon containing polymer content of from 1 to 15% by weight, preferably 2 to 10% by weight, particularly preferably 3 to 8% by weight. In a preferred embodiment, the coated titanium dioxide nanoparticles have a methicone or methicone/dimethicone copolymer content of 3 to 10% by weight, preferably 4 to 7% by weight, particularly preferably 4.5 to 6.5% by weight. The zinc dioxide particles have usually a silicon containing polymer content of from 0.1 to 15% by weight, preferably 0.3 to 9% by weight, particularly preferably 0.5 to 5% by weight. The percentages by weight refer to the total weight of the corresponding coated metal oxide nanoparticles.

The coated metal oxide nanoparticles have usually an inorganic oxide content of 1 to 20% by weight, preferably 3 to 15% by weight, particularly preferably 5 to 10% by weight. In a preferred embodiment, the coated metal oxide nanoparticles have a silicon dioxide content of from 4 to 10% by weight, preferably 5 to 9% by weight, particularly preferably 6.5 to 8.5% by weight. In another preferred embodiment, the coated metal oxide nanoparticles have an aluminum oxide content of from 0.5 to 15% by weight, preferably 1 to 10% by weight, particularly preferably 2 to 5% by weight. The titanium dioxide particles have usually a silicon dioxide content of from 4 to 10% by weight, preferably 5 to 9% by weight, particularly preferably 6.5 to 8.5% by weight, where the percentages refer to the total weight of the coated titanium dioxide particles. In general, the titanium dioxide particles have an aluminum oxide content of from 1 to 10% by weight, preferably 1 to 5% by weight, particularly preferably 2.5 to 4.5% by weight, where the percentages refer to the total weight of the coated titanium dioxide particles.

Coated iron oxide particles are sold, for example, by the company Arnaud under the names "Nanogard WCD 2008 (FE 45B FN)", "Nanogard WCD 2009 (FE 45B 556)", "Nanogard FE 45 BL 345" and "Nanogard FE 45 BL" or by the company BASF under the name "Transparent Iron Oxide".

Mention may also be made of mixtures of metal oxides, especially of titanium dioxide and of cerium dioxide, including the silica-coated equal-weight mixture of titanium dioxide and of cerium dioxide, sold by the company Ikeda under the name "Sunveil A", and also the alumina, silica and silicone-coated mixture of titanium dioxide and of zinc dioxide, such as the product "M 261" sold by the company Kemira, or the alumina, silica and glycerol-coated mixture of titanium dioxide and of zinc dioxide, such as the product "M 211" sold by the company Kemira.

In a preferred embodiment, the metal oxide comprises less than 0.05 mol %, preferably less than 0.01 mol %, more preferably less than 0.005 mol %, and especially no dopant. Suitable dopants are known, for example from WO2005/072680, page 42, second paragraph. Examples are cations of manganese, vanadium, chromium or iron.

The total amount of coated metal oxide nanoparticles in the agrochemical formulation is in general 0.5 to 20 wt %, preferably 2 to 15 wt % and more preferably 4 to 12 wt %.

Organic UV photoprotective filters are understood as meaning organic substances which are able to absorb ultraviolet rays and give off the absorbed energy again in the form of longer-wave radiation, e.g. heat. The term "Organic UV photoprotective filter" relates to one type or a mixture of different types of said compounds. The organic substances may be oil-soluble or water-soluble or they may be bound to a polymer. The photoprotective filters may be UV-A and UV-B filters, preferably UV-B filters. Typically, the photoprotective filters are colorless to light yellow compounds. Preferably, the photoprotective filters can not be detected visually at the applied concentration.

UV-B filters which may be used are, for example, the following substances:
  3-benzylidenecamphor and derivatives thereof, e.g. 3-(4-methylbenzylidene)camphor;
  4-aminobenzoic acid derivatives, preferably 2-ethylhexyl 4-(dimethylamino)benzoate, 2-octyl 4-(dimethylamino)benzoate and amyl 4-(dimethylamino)benzoate;
  esters of cinnamic acid, preferably 2-ethylhexyl 4-methoxycinnamate, propyl 4-methoxycinnamate, isoamyl 4-methoxycinnamate, isopentyl 4-methoxycinnamate, 2-ethylhexyl 2-cyano-3-phenylcinnamate(otocrylene);
  esters of salicylic acid, preferably 2-ethylhexyl salicylate, 4-isopropylbenzyl salicylate, homomenthyl salicylate;
  derivatives of benzophenone, preferably 2-hydroxy-4-methoxybenzophenone, 2-hydroxy-4-methoxy-4'-methylbenzophenone, 2,2'-dihydroxy-4-methoxybenzophenone;
  esters of benzalmalonic acid, preferably 2-ethylhexyl 4-methoxybenzmalonate;
  triazine derivatives, such as 2,4,6-trianilino(p-carbo-2'-ethyl-1'-hexyloxy)-1,3,5-triazine (octyltriazone) and dioctylbutamidotriazone (Uvasorb® HEB).
  Propane-1,3-diones, such as, for example, 1-(4-tert-butylphenyl)-3-(4'-methoxyphenyl)propane-1,3-dione.
  2-phenylbenzimidazole-5-sulfonic acid and alkali metal, alkaline earth metal, ammonium, alkylammonium, alkanolammonium and glucammonium salts thereof;
  sulfonic acid derivatives of benzophenones, preferably 2-hydroxy-4-methoxybenzo-phenone-5-sulfonic acid and its salts;
  sulfonic acid derivatives of 3-benzylidenecamphor, such as, for example, 4-(2-oxo-3-bornylidenemethyl)benzenesulfonic acid and 2-methyl-5-(2-oxo-3-bornylidene) sulfonic acid and salts thereof.

Preferred UV-B filters are derivatives of benzophenone.
Suitable UV-A filters are:
  derivatives of benzoylmethane, such as, for example, 1-(4'-tert-butylphenyl)-3-(4'-methoxyphenyl)propane-1,3-dione, 4-tert-butyl-4'-methoxydibenzoylmethane or 1-phenyl-3-(4'-isopropylphenyl)propane-1,3-dione;
  Aminohydroxy-substituted derivatives of benzophenones, such as, for example, N,N-diethylaminohydroxybenzoyl-n-hexylbenzoate.

The UV-A and UV-B filters can of course also be used in mixtures.

The total amount of organic UV photoprotective filter in the agrochemical formulation is in general 0.5 to 30 wt %, preferably 2 to 20 wt %, and more preferably 5 to 15 wt %. The weight ratio of the organic UV photoprotective filter to the coated metal oxide nanoparticles is usually in a range of 10:1 to 1:10, preferably 5:1 to 1:5, more preferably 3:1 to 1:2.

The weight ratio of the pesticide to the total mass of the organic UV photoprotective filter and the coated metal oxide nanoparticles is usually in the range of 50:1 to 1:10, preferably 20:1 to 1:2, and most preferably 10:1 to 1:1.

The agrochemical formulation may also comprise one or more antioxidants. Preferably, the agrochemical formulation comprises an antioxidants. Antioxidants are, for example, amino acids (e.g. glycine, histidine, tyrosine, tryptophan) and derivatives thereof, imidazole and imidazole derivatives (e.g. urocanic acid), peptides, such as, for example, D,L-carnosine, D-carnosine, L-carnosine and derivatives thereof (e.g. anserine), carotenoids, carotenes (e.g. α-carotene, β-carotene, lycopene) and derivatives thereof, lipoic acid and derivatives thereof (e.g. dihydrolipoic acid), aurothioglucose, propylthiouracil and further thio compounds (e.g. thioglycerol, thiosorbitol, thioglycolic acid, thioredoxin, glutathione, cysteine, cystine, cystamine and the glycosyl, N-acetyl, methyl, ethyl, propyl, amyl, butyl, lauryl, palmitoyl, oleyl, γ-linoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol/kg to µmol/kg), also metal chelating agents (e.g. α-hydroxy fatty acids, EDTA, EGTA, phytic acid, lactoferrin), α-hydroxy acids (e.g. citric acid, lactic acid, malic acid), humic acids, bile acid, bile extracts, gallic esters (e.g. propyl, octyl and dodecyl gallate), flavonoids, catechins, bilirubin, biliverdin and derivatives thereof, unsaturated fatty acids and derivatives thereof (e.g. γ-linolenic acid, linoleic acid, arachidonic acid, oleic acid), folic acid and derivatives thereof, hydroquinone and derivatives thereof (e.g. arbutin), ubiquinone and ubiquinol, and derivatives thereof, vitamin C and derivatives thereof (e.g. ascorbyl palmitate, stearate, dipalmitate, acetate, Mg ascorbyl phosphates, sodium and magnesium ascorbate, disodium ascorbyl phosphate and sulfate, potassium ascorbyl tocopheryl phosphate, chitosan ascorbate), isoascorbic acid and derivatives thereof, tocopherols and derivatives thereof (e.g. tocopheryl acetate, linoleate, oleate and succinate, tocophereth-5, tocophereth-10, tocophereth-12, tocophereth-18, tocophereth-50, tocophersolan), vitamin A and derivatives (e.g. vitamin A palmitate), the coniferyl benzoate of benzoin resin, rutin, rutinic acid and derivatives thereof, disodium rutinyl disulfate, cinnamic acid and derivatives thereof (e.g. ferulic acid, ethyl ferulate, caffeeic acid), kojic acid, chitosan glycolate and salicylate, butylhydroxytoluene, butylhydroxyanisol, nordihydroguaiacic acid, nordihydroguaiaretic acid, trihydroxybutyrophenone, uric acid and derivatives thereof, mannose and derivatives thereof, selenium and selenium derivatives (e.g. selenomethionine), stilbenes and stilbene derivatives (e.g. stilbene oxide, trans-stilbene oxide). According to the invention, suitable derivatives (salts, esters, sugars, nucleotides, nucleosides, peptides and lipids) and mixtures of these specified active ingredients or plant extracts (e.g. teatree oil, rosemary extract and rosemarinic acid) which comprise these antioxidants can be used. In general, mixtures of the aforementions antioxidants are possible.

Preferred antioxidants are tocopherols, butylhydroxytoluene and butylhydroxyanisol.

The total amount of antioxidants in the agrochemical formulation is in general 0-20% by weight, preferably 0.05-10% by weight, in particular 0.1-5% by weight and very particularly preferably 0.1 to 2% by weight.

The agrochemical formulation may additionally comprise radical scavengers. In general, most antioxidants such as butylhydroxytoluene and butylhydroxyanisol also act as radical scavengers. Further examples for radical scavengers are so called Hindered Amine Light Stabilizer (HALS), e.g. N,N'-1,6-hexanediylbis(N-(2,2,6,6-tetramethyl-piperidinyl-formamide (commercially available as Uvinul® 4050H from BASF SE), 1-acetyl-4-(3-dodecyl-2,5-dioxo-1-pyrrolidinyl)-2,2,6,6-tetramethyl-piperidine (Sanduvor® 3058 Liquid from Clariant), bis(1-octyloxy-2,2,6,-tetramethyl-4-piperidyl)sebacate (commercially available as Tinuvin® 123 from Ciba), Bis(1,2,2,6,6-pentamethyl-4-piperidyl)sebacate (commercially available as Tinuvin® 292 from Ciba). Preferred radical scavengers are hindered amine light stabilizers.

The total amount of radical scavenger in the agrochemical formulation is in general 0-20% by weight, preferably 0.05-10% by weight, in particular 0.1-5% by weight.

Optionally, the agrochemical formulation may additionally comprise uncoated metal oxide particles. These uncoated metal oxide may be chosen from the group of oxides of zinc (e.g. ZnO), iron (e.g. $Fe_2O_3$), zirconium (e.g. $ZrO_2$), silicon (e.g. $SiO_2$), manganese (e.g. MnO), aluminum (e.g. alumina $Al_2O_3$), cerium (e.g. $Ce_2O_3$), mixed oxides of the corresponding metals, and mixtures of such oxides. Preferred is zinc oxide. The total amount of uncoated metal oxide particles in the agrochemical formulation is in general 0 to 30 wt %, preferably 2 to 20 wt %, and more preferably 5 to 15 wt %. In a preferred embodiment, the agrochemical formulation is essentially free, preferably free, of uncoated metal oxide particles.

The agrochemical formulation according to the invention may optionally comprise formulation auxiliaries. The term "formulation auxiliaries" within the meaning of the invention is auxiliaries suitable for the formulation of pesticides, such as further solvents and/or carriers and/or surfactants (ionic and/or non-ionic surfactants, adjuvants, dispersing agents) and/or preservatives and/or antifoaming agents and/or anti-freezing agents.

Examples of suitable solvents are water, aromatic solvents (for example Solvesso products, xylene), paraffins (for example mineral oil fractions such as kerosene or diesel oil), coal tar oils and oils of vegetable or animal origin, aliphatic, cyclic and aromatic hydrocarbons, for example toluene, xylene, paraffin, tetrahydronaphthalene, alkylated naphthalenes or their derivatives, alcohols (for example methanol, butanol, pentanol, benzyl alcohol, cyclohexanol), ketones (for example cyclohexanone, gamma-butyrolactone), pyrrolidones (NMP, NEP, NOP), acetates (glycol diacetate), glycols, fatty acid dimethylamides, fatty acids and fatty acid esters, isophorone and dimethylsulfoxide. In principle, solvent mixtures may also be used.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ethers, ethoxylated isooctylphenol, octylphenol, nonylphenol, alkylphenol polyglycol ethers, tributylphenyl polyglycol ethers, tristearylphenyl polyglycol ethers, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Examples of suitable carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders, polyvinylpyrrolidone and other solid carriers.).

Also anti-freezing agents such as glycerin, ethylene glycol, hexylene glycol, propylene glycol and bactericides such as can be added to the formulation.

Suitable antifoaming agents are for example antifoaming agents based on silicon or magnesium stearate.

Suitable preservatives are for example 1,2-benzisothiazolin-3-one and/or 2-Methyl-2H-isothiazol-3-one or sodium benzoate or benzoic acid.

The term "pesticide" within the meaning of the invention states that one or more compounds can be selected from the group consisting of fungicides, insecticides, nematicides, herbicide and/or safener or growth regulator, preferably from the group consisting of fungicides, insecticides or nematicides. Also mixtures of pesticides of two or more the aforementioned classes can be used. The skilled artisan is familiar with such pesticides, which can be, for example, found in the Pesticide Manual, 13th Ed. (2003), The British Crop Protection Council, London.

The following list of pesticides is intended to illustrate the possible combinations, but not to impose any limitation:

The fungicide can be selected from the group consisting of
A) strobilurins
    azoxystrobin, dimoxystrobin, enestroburin, fluoxastrobin, kresoxim-methyl, metominostrobin, orysastrobin, picoxystrobin, pyraclostrobin, pyribencarb, trifloxystrobin, 2-(2-(6-(3-chloro-2-methyl-phenoxy)-5-fluoro-pyrimidin-4-yloxy)-phenyl)-2-methoxyimino-N-methyl-acetamide, 3-methoxy-2-(2-(N-(4-methoxyphenyl)-cyclopropane-carboximidoylsulfanylmethyl)-phenyl)-acrylic acid methyl ester, methyl(2-chloro-5-[1-(3-methylbenzyloxyimino)ethyl]benzyl)carbamate and 2-(2-(3-(2,6-dichlorophenyl)-1-methyl-allylideneaminooxymethyl)-phenyl)-2-methoxyimino-N-methyl-acetamide;

B) carboxamides carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penthiopyrad, tecloftalam, thifluzamide, tiadinil, 2-amino-4-methyl-thiazole-5-carboxanilide, 2-chloro-N-(1,1,3-trimethyl-indan-4-yl)-nicotinamide, N-(2',4'-difluorobiphenyl-2-yl)-3-difluoromethyl-1-methyl-1H-pyrazole-4-carboxamide, N-(2',4'-dichlorobiphenyl-2-yl)-3-difluoromethyl-1-methyl-1H-pyrazole-4-carboxamide, N-(2',5'-difluorobiphenyl-2-yl)-3-difluoromethyl-1-methyl-1H-pyrazole-4-carboxamide, N-(2',5'-dichlorobiphenyl-2-yl)-3-difluoromethyl-1-methyl-1H-pyrazole-4-carboxamide, N-(3',5'-difluorobiphenyl-2-yl)-3-difluoromethyl-1-methyl-1H-pyrazole-4-carboxamide, N-(3'-fluorobiphenyl-2-yl)-3-difluoromethyl-1-methyl-1H-pyrazole-4-carboxamide, N-(3'-chlorobiphenyl-2-yl)-3-difluoromethyl-1-methyl-1H-pyrazole-4-carboxamide, N-(2'-fluorobiphenyl-2-yl)-3-difluoromethyl-1-methyl-1H-pyrazole-4-carboxamide, N-(2'-chlorobiphenyl-2-yl)-3-difluoromethyl-1-methyl-1H-pyrazole-4-carboxamide, N-(3',5'-dichlorobiphenyl-2-yl)-3-difluoromethyl-1-methyl-1H-pyrazole-4-carboxamide, N-(3',4',5'-trifluorobiphenyl-2-yl)-3-difluoromethyl-1-methyl-1H-pyrazole-4-carboxamide, N-(2',4',5'-trifluorobiphenyl-2-yl)-3-difluoromethyl-1-methyl-1H-pyrazole-4-carboxamide, N-[2-(1,1,2,3,3,3-hexafluoropropoxy)-phenyl]-3-difluoromethyl-1-methyl-1H-pyrazole-4-carboxamide, N-[2-(1,1,2,2-tetrafluoroethoxy)-phenyl]-3-difluoromethyl-1-methyl-1H-pyrazole-4-carboxamide, N-(4'-trifluoromethyl-thiobiphenyl-2-yl)-3-difluoromethyl-1-methyl-1H-pyrazole-4-carboxamide, N-(2-(1,3-dimethyl-butyl)-phenyl)-1,3-dimethyl-5-fluoro-1H-pyrazole-4-carboxamide, N-(2-(1,3,3-trimethyl-butyl)-phenyl)-1,3-dimethyl-5-fluoro-1H-pyrazole-4-carboxamide, N-(4'-chloro-3',5'-difluoro-biphenyl-2-yl)-3-difluoromethyl-1-methyl-1H-pyrazole-4-carboxamide, N-(4'-chloro-3',5'-difluoro-biphenyl-2-yl)-3-trifluoromethyl-1-methyl-1H-pyrazole-4-carboxamide, N-(3',4'-dichloro-5'-fluoro-biphenyl-2-yl)-3-trifluoromethyl-1-methyl-1H-pyrazole-4-carboxamide, N-(3',5'-difluoro-4'-methyl-biphenyl-2-yl)-3-difluoromethyl-1-methyl-1H-pyrazole-4-carboxamide, N-(3',5'-difluoro-4'-methyl-biphenyl-2-yl)-3-trifluoromethyl-1-methyl-1H-pyrazole-4-carboxamide, N-(2-bicyclopropyl-2-yl-phenyl)-3-difluoromethyl-1-methyl-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoromethyl-1-methyl-1H-pyrazole-4-carboxamide, N-[1,2,3,4-tetrahydro-9-(1-methylethyl)-1,4-methano-naphthalen-5-yl]-3-(difluoromethyl)-1-methyl-1H-pyrazole-4-carboxamide;

carboxylic morpholides: dimethomorph, flumorph;

benzoic acid amides: flumetover, fluopicolde, fluopyram;

other carboxamides: carpropamid, dicyclomet, mandiproamid, oxytetracyclin, silthiofarm and N-(6-methoxy-pyridin-3-yl)cyclopropanecarboxylic acid amide;

C) azoles triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-(4-chloro-phenyl)-2-([1,2,4]triazol-1-yl)-cycloheptanol;

imidazoles: cyazofamid, imazalil, pefurazoate, prochloraz, triflumizol;

benzimidazoles: benomyl, carbendazim, fuberidazole, thiabendazole;

others: ethaboxam, etridiazole, hymexazole and 2-(4-chloro-phenyl)-N-[4-(3,4-dimethoxy-phenyl)-isoxazol-5-yl]-2-prop-2-ynyloxy-acetamide;

D) heterocyclic compounds pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetra-chloro-4-methanesulfonyl-pyridine, 3,4,5-trichloropyridine-2,6-di-carbonitrile, N-(1-(5-bromo-3-chloro-pyridin-2-yl)-ethyl)-2,4-dichloronicotinamide, N-[(5-bromo-3-chloro-pyridin-2-yl)-methyl]-2,4-dichloro-nicotinamide;

pyrimidines: bupirimate, cyprodinil, diflumetorim, fenarimol, ferimzone, mepanipyrim, nitrapyrin, nuarimol, pyrimethanil;

piperazines: triforine;

pyrroles: fenpiclonil, fludioxonil;

morpholines: aldimorph, dodemorph, dodemorph-acetate, fenpropimorph, tridemorph;

piperidines: fenpropidin;

dicarboximides: fluoroimid, iprodione, procymidone, vinclozolin;

non-aromatic 5-membered heterocycles: famoxadone, fenamidone, octhilinone, probenazole, 5-amino-2-isopropyl-3-oxo-4-ortho-tolyl-2,3-dihydro-pyrazole-1-carbothioic acid S-allyl ester;

others: acibenzolar-S-methyl, amisulbrom, anilazin, blasticidin-S, captafol, captan, chinomethionat, dazomet, debacarb, diclomezine, difenzoquat, difenzoquat-methyl-sulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole, 5-chloro-7-(4-methyl-piperidin-1-yl)-6-(2,4,6-trifluorophenyl)-[1,2,4]triazolo[1,5-a]pyrimidine, 6-(3,4-dichloro-phenyl)-5-methyl-[1,2,4]triazolo[1,5-a]pyrimidine-7-ylamine, 6-(4-tert-butyl-phenyl)-5-methyl-[1,2,4]triazolo[1,5-a]pyrimidine-7-ylamine, 5-methyl-6-(3,5,5-trimethyl-hexyl)-[1,2,4]triazolo[1,5-a]pyrimidine-7-ylamine, 5-methyl-6-octyl-[1,2,4]triazolo[1,5-a]pyrimidine-7-ylamine, 6-methyl-5-octyl-[1,2,4]triazolo[1,5-a]pyrimidine-7-ylamine, 6-ethyl-5-octyl-[1,2,4]triazolo[1,5-a]pyrimidine-7-ylamine, 5-ethyl-6-octyl-[1,2,4]triazolo[1,5-a]pyrimidine-7-ylamine, 5-ethyl-6-(3,5,5-trimethyl-hexyl)-[1,2,4]triazolo[1,5-a]pyrimidine-7-ylamine, 6-octyl-5-propyl-[1,2,4]triazolo[1,5-a]pyrimidine-7-ylamine, 5-methoxymethyl-6-octyl-[1,2,4]triazolo[1,5-a]pyrimidine-7-ylamine, 6-octyl-5-trifluoromethyl-[1, 2,4]triazolo[1,5-a]pyrimidine-7-ylamine and 5-trifluoromethyl-6-(3,5,5-trimethyl-hexyl)-[1,2,4]triazolo[1,5-a]pyrimidine-7-ylamine;

E) carbamates thio- and dithiocarbamates: ferbam, mancozeb, maneb, metam, methasulphocarb, metiram, propineb, thiram, zineb, ziram;

carbamates: benthiavalicarb, diethofencarb, flubenthiavalicarb, iprovalicarb, propamocarb, propamocarb hydrochlorid, valiphenal and N-(1-(1-(4-cyano-phenyl)-ethanesulfonyl)-but-2-yl)carbamic acid-(4-fluorophenyl)ester;

F) other active substances guanidines: guanidine, dodine, dodine free base, guazatine, guazatine-acetate, iminoctadine, iminoctadine-triacetate, iminoctadine-tris(albesilate);

antibiotics: kasugamycin, kasugamycin hydrochloride-hydrate, streptomycin, polyoxine, validamycin A;

nitrophenyl derivates: binapacryl, dinobuton, dinocap, nitrthal-isopropyl, tecnazen, organometal compounds: fentin salts, such as fentin-acetate, fentin chloride or fentin hydroxide;

sulfur-containing heterocyclyl compounds: dithianon, isoprothiolane;

organophosphorus compounds: edifenphos, fosetyl, fosetyl-aluminum, iprobenfos, phosphorus acid and its salts, pyrazophos, tolclofos-methyl;

organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methyl-benzenesulfonamide;

inorganic active substances: Bordeaux mixture, copper acetate, copper hydroxide, copper oxychloride, basic copper sulfate, sulfur;

others: biphenyl, bronopol, cyflufenamid, cymoxanil, diphenylamin, metrafenone, mildiomycin, oxin-copper, prohexadione-calcium, spiroxamine, tolylfluanid, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-formamidine, N'-(2-methyl-5-trifluoromethyl-4-(3-trimethylsilanyl-propoxy)-phenyl)-N-ethyl-N-methyl formamidine and N'-(5-difluoromethyl-2-methyl-4-(3-trimethylsilanyl-propoxy)-phenyl)-N-ethyl-N-methyl formamidine.

The herbicide can be selected from the group consisting of acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

Bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bomoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxyacetic acid (2,4-D), 2,4-DB, dichlorprop, MCPA, MCPA-thioethyl, MCPB, Mecoprop;

pyrazines: chloridazon, flufenpyr-ethyl, fluthiacet, norflurazon, pyridate;

pyridines: aminopyralid, clopyralid, diflufenican, dithiopyr, fluridone, fluroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bromacil, bromobutide, butafenacil, butamifos, cafenstrole, carfentrazone, cinidon-ethlyl, chlorthal, cinmethylin, clomazone, cumyluron, cyprosulfamide, dicamba, difenzoquat, diflufenzopyr, Drechslera monoceras, endothal, ethofumesate, etobenzanid, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, 4-hydroxy-3-[2-(2-methoxy-ethoxymethyl)-6-trifluoromethyl-pyridine-3-carbonyl]-bicyclo[3.2.1]oct-3-en-2-one, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

The insecticide can be selected from the group consisting of
- organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;
- carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;
- pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;
- insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;
- nicotinic receptor agonists/antagonists compounds: clothianidin, dinotefuran, imidacloprid, thiamethoxam, nitenpyram, acetamiprid, thiacloprid, 1-(2-chloro-thiazol-5-ylmethyl)-2-nitrimino-3,5-dimethyl-[1,3,5]triazinane;
- GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;
- macrocyclic lactone insecticides: abamectin, emamectin, milbemectin, lepimectin, spinosad, spinetoram;
- mitochondrial electron transport inhibitor (METI) I acaricides: fenazaquin, pyridaben, tebufenpyrad, tolfenpyrad, flufenerim;
- METI II and III compounds: acequinocyl, fluacyprim, hydramethylnon;
- Uncouplers: chlorfenapyr;
- oxidative phosphorylation inhibitors: cyhexatin, diafenthiuron, fenbutatin oxide, propargite;
- moulting disruptor compounds: cryomazine;
- mixed function oxidase inhibitors: piperonyl butoxide;
- sodium channel blockers: indoxacarb, metaflumizone;
- others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluron, and pyrifluquinazon.

The growth regulator can be selected from the group consisting of abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole.

In a preferred embodiment, the pesticide is sensitive to UV light. The sensitivity may be detected by simple tests, in which a pesticide is exposed to UV light for a certain time. Subsequently, residual pesticide, which was not decomposed, may be quantified.

Preferred herbicides are napropamid, propamil, Bentazone, Paraquat dichlorid, cycloxydim, sethoxydim, Ethalfluralin, Oryzalin, Pendimethalin, Trifluralin, Acifluren, Aclonifen, Fomesafen, oxyfluoren, Ioxynil, Imazetapyr, Imazaquin, chloridazon, norflurazon, Thiazopyr, Triclopyr, dithiopyr, Diflufenican, picolinafen, amidosulfuron, Molinate, vernolate, Promethon, Metribuzin, azafenidin, Carfentrazone-ethyl, sulfentrazone, metoxuron, monolinuron, Fluchloralin and Flurenol.

Preferred fungicides are cyprodinil, Fuberidazol, dimethomorph, procloraz, Triflumizol, tridemorph, edifenfos, Fenarimol, Nuarimol, ethirimol, quinoxylen, Dithianon, Metominostrobin, Trifloxystrobin, Dichlofluamid, Bromuconnazol and myclobutanil.

Preferred insecticides are Acephate, Azinphos-Ethyl, Azinphos-Methyl, Isofenphos, Chlorpyriphos-Methyl, Dimethylvinphos, Phorate, Phoxim, Prothiofos, cyhexatin, alanycarb, Ethiofencarb, pirimicarb, Thiodicarb, Fipronil, bioallethrin, bioresmethin, Deltamethrin, fenpropathin, Flucythrinate, Tau fluvalinate, cypermethrin, Zeta cypermethrin, resmethin, tefluthrin, Lambda cyhalothrin and hydramethylnon. In another preferred embodiment, the insecticide is metaflumizone or alpha-cypermethrin.

The pesticide is most preferably metaflumizone or alpha-cypermethrin, especially metaflumizone.

The agrochemical formulation according to the invention is prepared by a method, wherein a pesticide, an organic UV-filter and a coated metal oxide nanoparticle are mixed. In general, said compounds may be mixed in any order in a single or multistep mixing. A pesticide, an organic UV-filter and a coated metal oxide nanoparticle may be added together or individually to any process for the preparation of agrochemical formulations. One or more of said compounds may be added to the agrochemical formulation and the residual compounds to the tank mix comprising said agrochemical formulation.

Examples of suitable agrochemical formulation are liquid formulations such as EC (Emulsifiable concentrate) formulation; SL or LS (Soluble concentrate) formulation; EW (Emulsion, oil in water) formulation; ME (Microemulsion) formulation; MEC (Microemulsifiable concentrates) formulation; CS (Capsule suspension) formulation; TK (Technical concentrate) formulation; OD (oil based suspension concentrate) formulation; SC (suspension concentrate) formulation; SE (Suspo-emulsion) formulation; ULV (Ultra-low volume liquid) formulation; SO (Spreading oil) formulation; AL (Any other liquid) formulation; LA (Lacquer) formulation; DC (Dispersible concentrate) formulation; or solid formulations such as WG (Water dispersible granules) formulation; TB (Tablet) formulation; FG (Fine granule) formulation; MG (Microgranule) formulation; SG (soluble Granule). Preferred liquid formulations are EC, SL, LS, EW, ME, MEC, TK, OD, SC, SE, ULV, SO, AL, LA and DC.

Preferred agrochemical formulations are liquid formulations. More preferably, the liquid agrochemical formulation comprises a pesticide, which is dissolved, emulsified as droplets or suspended as matrix particles. Even more preferably, the liquid agrochemical formulation comprises a pesticide, which is dissolved or emulsified as droplets. The term "matrix particles" refers to particles, in which the pesticide is homogenously distributed throughout the particle. For comparison, in encapsulated pesticide particles (which are not matrix particles) the pesticide is concentrated in the core and thus often protected by a polymer wall from UV radiation.

The above-referred formulations can be used as such or use forms prepared there from, for example in the form of directly sprayable solutions, powders, suspensions or dispersions, emulsions, oil dispersions, pastes, dustable products, materials for spreading, or granules, by means of spraying, atomizing, dusting, spreading or pouring.

The use forms depend entirely on the intended purposes; it is intended to ensure in each case the finest possible distribution of the pesticid(es) and polymer according to the invention.

Aqueous use forms can be prepared also from emulsion concentrates, pastes or wettable powders (sprayable powders, oil dispersions) by adding a suitable solvent, for example water.

The components can be used individually or already partially or completely mixed with one another to prepare the composition according to the invention. It is also possible for them to be packaged and used further as combination composition such as a kit of parts. In one embodiment of the invention, the kits may include one or more, including all, components that may be used to prepare a subject agrochemical composition. E. g., kits may include a pesticide component(s) and/or an organic UV photoprotective filter component and/or a coated metal oxide nanoparticles component. One or more of the components may already be combined together or pre-formulated. In those embodiments where more than two components are provided in a kit, the components may already be combined together and as such are packaged in a single container such as a vial, bottle, can, pouch, bag or canister. In other embodiments, two or more components of a kit may be packaged separately, i. e., not pre-formulated. As such, kits may include one or more separate containers such as vials, cans, bottles, pouches, bags or canisters, each container containing a separate component for an agrochemical composition. In both forms, a component of the kit may be applied separately from or together with the further components or as a component of a combination composition according to the invention for preparing the composition according to the invention.

In a preferred embodiment, the invention relates to a kit of parts, comprising as separate components
    A) a composition comprising an organic UV photoprotective filter and a coated metal oxide nanoparticles, and
    B) a pesticide
for combined application in a method of combating undesired vegetation, harmful insects and/or phytopathogenic fungi.

The composition A) comprising an organic UV photoprotective filter and a coated metal oxide nanoparticles may be prepared by mixing said compounds. Optionally, formulation auxiliaries may be added. Said composition may be solid or liquid, preferably liquid. Component B) comprising the pesticide is in general present in an agrochemical formulation or in a diluted agrochemical formulation. Preferably, the separate components A) and B) are combined in the tank mix. Usually, said components are applied at the same time or within 48 h, preferably 24 h, more preferably 12 h, most preferably 6 h to undesired vegetation, harmful insects and/or phytopathogenic fungi. Preferably, they are applied at the same time.

All embodiments of the above-mentioned application are herein below referred to as "formulation according to the present invention".

The present invention also relates to a use of a mixture of an organic UV photoprotective filter and coated metal oxide nanoparticles in agrochemical formulations. A further embodiment is the use of the formulation according to the present invention in agrochemical formulations.

The invention relates also to a use of the formulation according to the present invention for stabilizing a pesticide against UV irradiation.

Further on, the invention relates to a method of combating harmful insects and/or phytopathogenic fungi, which comprises contacting plants, soil or habitat of plants in or on which the harmful insects and/or phytopathogenic fungi are growing or may grow, plants or soil to be protected from attack or infestation by said harmful insects and/or phytopathogenic fungi with an effective amount of the formulation according to the present invention. The formulations according to the present invention can therefore be used for the control of a multitude of phytopathogenic fungi or insects on various cultivated plants or weeds in, such as wheat, rye, barley, oats, rice, corn, grass, bananas, cotton, soy, coffee, sugar cane, vines, fruits and ornamental plants, and vegetables, such as cucumbers, beans, tomatoes, potatoes and cucurbits.

The present invention also relates to a method of controlling undesired vegetation, which comprises allowing a herbicidal effective amount of the formulation according to the present invention to act on plants, their habitat. The control of undesired vegetation is understood as meaning the destruction of weeds. Weeds, in the broadest sense, are understood as meaning all those plants which grow in locations where they are undesired.

The formulations according to the present invention can therefore be used for the control of a multitude of phytopathogenic fungi or insects on various cultivated plants or weeds in, such as wheat, rye, barley, oats, rice, corn, grass, bananas, cotton, soy, coffee, sugar cane, vines, fruits and ornamental plants, and vegetables, such as cucumbers, beans, tomatoes, potatoes and cucurbits, and on the seeds of these plants.

Thus, the formulations according to the present invention compositions according to the present invention are suitable for controlling common harmful plants in useful plants, in particular in crops such as oat, barley, millet, corn, rice, wheat, sugar cane, cotton, oilseed rape, flax, lentil, sugar beet, tobacco, sunflowers and soybeans or in perennial crops.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e. g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e. g. WO 92/00377); glutamine synthetase (GS) inhibitors, such as glufosinate (see e.g. EP-A 242 236, EP-A 242 246) or oxynil herbicide (see e. g. U.S. Pat. No. 5,559,024) as a result of conventional methods of breeding or genetic engineering. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The term phytopathogenic fungi includes but is not limited to the following species: *Alternaria* species on vegetables, rapeseed, sugar beet and fruit and rice (for example *A. solani* or *A. alternata* on potato and other plants); *Aphanomyces* species on sugar beet and vegetables; *Bipolaris* and *Drech-* slera species on corn, cereals, rice and lawns (for example *D. teres* on barley, *D. tritci-repentis* on wheat); *Blumeria graminis* (powdery mildew) on cereals; *Botrytis cinerea* (gray mold) on strawberries, vegetables, flowers and grapevines; *Bremia lactucae* on lettuce; *Cercospora* species on corn, soybeans, rice and sugar beet (for example *C. beticula* on sugar beet); *Cochliobolus* species on corn, cereals, rice (for example *Cochliobolus sativus* on cereals, *Cochliobolus miyabeanus* on rice); *Colletotricum* species on soybeans, cotton and other plants (for example *C. acutatum* on various plants); Esca on grapes caused by *Phaeoacremonium chlamydosporium, Ph. Aleophilum*, and *Formitipora punctata* (syn. *Phellinus punctatus*); *Exserohilum* species on corn; *Erysiphe cichoracearum* and *Sphaerotheca fuliginea* on cucurbits; *Fusarium* and *Verticillium* species (for example *V. dahliae*) on various plants (for example *F. graminearum* on wheat); *Gaeumanomyces graminis* on cereals; *Gibberella* species on cereals and rice (for example *Gibberella fujikuroi* on rice); Grainstaining complex on rice; *Helminthosporium* species (for example *H. graminicola*) on corn and rice; *Microdochium nivale* on cereals; *Mycosphaerella* species on cereals, bananas and peanuts (*M. graminicola* on wheat, *M. fijiesis* on bananas); *Phakopsara pachyrhizi* and *Phakopsara meibomiae* on soybeans; *Phomopsis* species on soybeans, sunflowers and grapevines (*P. viticola* on grapevines, *P. helianthii* on sunflowers); *Phytophthora infestans* on potatoes and tomatoes; *Plasmopara viticola* on grapevines; *Podosphaera leucotricha* on apples; *Pseudocercosporella herpotrichoides* on cereals; *Pseudoperonospora* species on hops and cucurbits (for example *P. cubenis* on cucumbers); *Puccinia* species on cereals, corn and asparagus (*P. triticina* and *P. striformis* on wheat, *P. asparagi* on asparagus); *Pyrenophora* species on cereals; *Pyricularia oryzae, Corticium sasakii, Sarocladium oryzae, S. attenuatum, Entyloma oryzae* on rice; *Pyricularia grisea* on lawns and cereals; *Pythium* spp. on lawns, rice, corn, cotton, rapeseed, sunflowers, sugar beet, vegetables and other plants; *Rhizoctonia*-species (for example *R. solani*) on cotton, rice, potatoes, lawns, corn, rapeseed, potatoes, sugar beet, vegetables and other plants; *Rhynchosporium secalis* e.g. on rye and barley; *Sclerotinia* species (for example *S. sclerotiorum*) on rapeseed, sunflowers and other plants; *Septoria tritici* and *Stagonospora nodorum* on wheat; *Erysiphe* (syn. *Uncinula necator*) on grapevines; *Setospaeria* species on corn and lawns; *Sphacelotheca reilinia* on corn; *Thievaliopsis* species on soybeans and cotton; *Tilletia* species on cereals; *Ustilago* species on cereals, corn and sugar beet and; *Venturia* species (scab) on apples and pears (for example *V. inaequalis* on apples). They are particularly suitable for controlling harmful fungi from the class of the *Oomycetes*, such as *Peronospora* species, *Phytophthora* species, *Plasmopara viticola* and *Pseudoperonospora* species.

The invention furthermore relates to a method for controlling undesirable vegetation in crops, in particular in crops of oat, barley, millet, corn, rice, wheat, sugar cane, cotton, oilseed rape, flax, lentil, sugar beet, tobacco, sunflowers and soybeans or in perennial crops, which comprises allowing a effective amount of a agrochemical formulation according to the present invention to act on plants, their habitat or on seed of said plants.

The invention furthermore relates to a method for controlling undesirable vegetation in crops which, by genetic engineering or by breeding, are resistant to one or more herbicides and/or fungicides and/or or to attack by insects, which comprises allowing a effective amount of a agrochemical formulation according to the present invention to act on plants, their habitat or on seed of said plants.

The control of undesired vegetation is understood as meaning the destruction of weeds. Weeds, in the broadest sense, are understood as meaning all those plants which grow in locations where they are undesired, for example:

Dicotyledonous weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum*.

Monocotyledonous weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus, Apera*.

The present invention provides several advantages: The decomposition of pesticides due to sunlight, especially ultraviolet (UV) light was reduced. The stability of agrochemical formulation of pesticides during storage and/or after application to the environment was increased. The pesticidal activity of agrochemical formulations after application to the environment was increased. There is no need for encapsulation of the pesticide in order to prevent UV damage. Even dissolved pesticides or suspended matrix particles are stabilized towards UV light. There is also no need for cumbersome doping of the metal oxide nanoparticles, which allows for use of cheap and commercially available metal oxide nanoparticles.

The invention is further illustrated but not limited by the following examples.

EXAMPLES

Emulsifier: Poly(ethylenglykol-block-propylenglykol-block-ethylenglykol), with a propylenglykol-block of a molar mass of 3250 g/mol and a total polymer mass of about 6500 g/mol (commercially available, e.g. from BASF SE as Pluronic® PE 10500)

Dispersant: Sodium salt of a phenolsulfonic acid-urea-formaldehyde-condensation product (commercially available, e.g. from BASF SE as Wettol® D1).

Biozide: Aqueous mixture of 2.5 wt % 2-methyl-4-isothiazolin-3-one (MIT) and 2.5 wt % 1,2-enzisothiazolin-3-on (BIT) (commercially available, e.g. from Thor as Acticide® MBS)

Titanium dioxide: Titanium dioxide particles with a coating of dimethoxydiphenylsilantriethoxycaprylsilan crosspolymer, silica and aluminum hydroxide; crystallite size 14-16 nm; rutil crystal structure; specific surface BET 100 m$^2$/g; 69-73 wt % content of titanium dioxide (commercially available, e.g. from BASF SE as T-Lite® MAX).

Zinc oxide: Zinc Oxide particles with a coating of dimethoxydiphenylsilane-triethoxycaprylylsilane crosspolymer, hydrated silica and aluminum hydroxide; 96-99 wt % micronized zin oxide, 1-4 wt % coating; particle size<0.2 μm; BET surface 12-24 m$^2$/g (commercially available, e.g. from BASF SE as Z-Cote® MAX).

Antifoaming agent: Silicone based antifoaming emulsion comprising 20 wt % nonionic silicone (commercially available, e.g. from Wacker as Silifoam SRE).

T150: Ethylhexyl triazone type photoprotective filter (2,4,6-Trianilino-p-(carbo-2'-ethyl-hexyl-1'-oxi)-1,3,5-triazin, CAS Nr. 88122-99-0; commercially available, e.g. from BASF SE as Uvinul® T150).

3040: 2-Hydroxy-4-methoxybenzophenone photoprotective filter (CAS Nr. 131-57-7; commercially available, e.g. from BASF SE as Uvinul® 3040).

Example 1

Suspension Concentrate

The suspension concentrates (SC) C-1 to C-3 (not according to the invention) and A (according to the invention) are obtained by grinding the below listed compounds in a Dispermat® (1 h at 3000 U/min). A homogenous, stable suspension is obtained, in which 90% of the solid particles have a particle size of less than 5 µm.

C-1: without organic UV filter, without coated titanium dioxide

C-2: with organic UV filter, without coated titanium dioxide

C-3: without organic UV filter, with coated titanium dioxide

A: with organic UV filter, with coated titanium dioxide

TABLE 1

|  | Examples for comparison (not according to the invention) | | | Example According to the invention |
|---|---|---|---|---|
|  | C-1 | C-2 | C-3 | A |
| Pesticide | 96 | 96 | 96 | 96 |
| 1,2-Propylen glycol | 67 | 67 | 67 | 67 |
| Emulsifier | 159 | 159 | 159 | 159 |
| Dispersant | 19 | 19 | 19 | 19 |
| Polydimethylsiloxan | 2 | 2 | 2 | 2 |
| Hydroxybenzophenon[a] | 0 | 143 | 0 | 48 |
| Titanium dioxide | 0 | 0 | 143 | 95 |
| Biozide | 2 | 2 | 2 | 2 |
| Xantham Gum | 3 | 3 | 3 | 3 |
| Water | 652 | 510 | 510 | 510 |
| Sum of listed parts | 1000 | 1000 | 1000 | 1000 |

[a] organic photoprotective filter

Example 2

Improvement of the Biological Activity

Peppercorns (*piper nigrum*) is treated with a diluted suspension concentrate of Example 1, wherein the concentration of pesticide is 300 or 500 ppm. The plants are kept in a greenhouse, which is penetrable for UV irradiation from sunlight. The plants are infested with green peach aphid (*Myzus persicae*) after 0 and 7 day (DAT=0 or 7). The mortality is determined 4 days after the infestation. The mortality of the green peach aphids is significantly higher when using the composition A compared to compositions C-1 to C-3.

Example 3

Damage to Plants/Phytotoxicity

The peppercorns of Example 2 are examined eight days after infestation with regard to damages to the plants. The plants are basically not damaged by composition A or by compositions C-1 to C-3.

Example 4

Suspension Concentrate

The suspension concentrates Comp-1 to Comp-58 not according to the invention) were obtained filling up a mixture of 100 g metaflumizone, 70 g propylene glycol, 167 g emulsifier, 20 g dispersant, 5 g antifoaming agent, 3 g xanthan gum, 2 g biozide, optionally an organic UV photoprotective filter and optionally coated metal oxide nanoparticles with water to a total volume of 1000 ml, subsequently mixing and grinding (on a Dispermat®, 1 h at 3000 U/min) it to form a homogeneous suspension. Details of the composition Comp-1 to Comp-5 are listed in Table 2. The samples 1-12 were prepared by mixing the samples Comp-1 to Comp-5 in a suitable amount, such that the concentrations were achieved as listed in Table 2. TiO$_2$ refers to titanium dioxide and ZnO refers to zinc oxide. The particle size D(4;3) of all samples was about 1.0 µm.

The samples 1-12 were stable on storage and no phase separation was observed. The particle size was observed during storage for two weeks at 54° C. No change in particle size was found and no aggregates were formed.

TABLE 2

| Sample | Metal oxide | Concentration metal oxide [g/l] | Photoprotective filter | Concentration photoprotective filter [g/l] |
|---|---|---|---|---|
| Comp-1 | — | — | — | — |
| Comp-2 | TiO$_2$ | 50 | — | — |
| Comp-3 | — | — | T150 | 50 |
| Comp-4 | — | — | 3040 | 50 |
| Comp-5 | ZnO | 50 | — | — |
| 1 | TiO$_2$ | 35 | T150 | 15 |
| 2 | TiO$_2$ | 35 | 3040 | 15 |
| 3 | TiO$_2$ | 25 | T150 | 25 |
| 4 | TiO$_2$ | 25 | 3040 | 25 |
| 5 | TiO$_2$ | 15 | T150 | 35 |
| 6 | TiO$_2$ | 15 | 3040 | 35 |
| 7 | ZnO | 35 | T150 | 15 |
| 8 | ZnO | 25 | T150 | 25 |
| 9 | ZnO | 15 | T150 | 35 |
| 10 | ZnO | 35 | 3040 | 15 |
| 11 | ZnO | 25 | 3040 | 25 |
| 12 | ZnO | 15 | 3040 | 35 |

Example 5

Residual Insecticidal Activity After UV Exposure

Lima bean plants (2 true-leaf stage) were used for metaflumizone treatments after terminals and cotyledons were removed. To simulate field treatment, plants were treated in an indoor spray chamber with a 3-nozzle row crop boom. The application volume was 300 L/ha, and for comparison of different formulations, metaflumizone was applied at a rate of 10 g/ha. After air-dried, treated plants were held at 26° C. under constant, 24 h/d light in a growth chamber equipped with a combination of fluorescent and UV bulbs. In the UV chamber, the radiation intensity of light in the UV range of 300-400 nm was measured at 39 Watt/m$^2$.

At 1, 4, 7 and 10 days after treatment (DAT), treated plants were removed from the lab and UV chambers for bioassay with insects to determine residual insecticidal activity of metaflumizone. First, leaves were cut from treated plants and each leaf was placed into a plastic petri dish topside-up onto water-moistened filter paper. Then 7 southern armyworm (*Spodoptera eridania*) larvae (3rd instars) were placed into each dish, and lids were placed on dishes to contain larvae. Each dish was a replication, and there were 4 replications per treatment. Dishes containing treated leaves and southern armyworm were held in the lab chamber under constant fluorescent lighting at 26° C., and mortality (dead+moribund) and feeding damage (visual estimation of % leaf surface damaged) was assessed 3 to 4 days later (table 3).

The data demonstrate that the compositions according to the invention have a higher residual activity of metaflumizone after exposure to UV light compared to the reference composition Comp-1 without titanium dioxide, zinc oxide or photoprotective filter.

The data also showed, that when only titanium dioxide (Comp-2) or zinc oxide (Comp-5) is added to Comp-1, there is rather a detrimental effect on residual activity compared to Comp-1.

Further on, the samples according to the invention had a rather low concentration of T150 or 3040 in a range of 15 to 35 g/l. Nevertheless, the residual activity of these samples was nearly as high or even higher compared to the samples containing only 3040 (Comp-3) or T150 (Comp-5), both at a rather high concentration of 50 g/l.

TABLE 3

| Sample | Comment | 1 DAT | 4 DAT | 7 DAT | 10 DAT | Cumulative |
|---|---|---|---|---|---|---|
| Comp-1 | — | 100 | 100 | 21 | 21 | 242 |
| Comp-2 | Only $TiO_2$ | 100 | 86 | 11 | 21 | 218 |
| Comp-3 | Only T150 | 100 | 100 | 46 | 57 | 303 |
| Comp-4 | Only 3040 | 100 | 100 | 32 | 21 | 253 |
| Comp-5 | Only ZnO | 100 | 86 | 18 | 36 | 240 |
| 1 | $TiO_2$ + T150 | 100 | 86 | 46 | 25 | 257 |
| 3 | $TiO_2$ + T150 | 100 | 100 | 61 | 64 | 325 |
| 2 | $TiO_2$ + 3040 | 100 | 100 | 64 | 46 | 310 |
| 4 | $TiO_2$ + 3040 | 100 | 64 | 57 | 57 | 278 |
| 6 | $TiO_2$ + 3040 | 100 | 100 | 32 | 25 | 257 |
| 7 | ZnO + T150 | 100 | 89 | 68 | 32 | 289 |
| 8 | ZnO + T150 | 100 | 96 | 75 | 57 | 328 |
| 9 | ZnO + T150 | 100 | 93 | 71 | 71 | 335 |
| 10 | ZnO + 3040 | 100 | 100 | 100 | 82 | 382 |
| 11 | ZnO + 3040 | 100 | 82 | 68 | 50 | 300 |
| 12 | ZnO + 3040 | 100 | 86 | 64 | 57 | 307 |

The invention claimed is:

1. An agrochemical formulation comprising a pesticide, an organic UV photoprotective filter and coated metal oxide nanoparticles, wherein the pesticide is a fungicide, insecticide, nematicide, herbicide, safener or growth regulator, and wherein the pesticide is dissolved, emulsified as droplets or suspended as matrix particles, wherein the weight ratio of the organic UV photoprotective filter to the metal oxide is in a range of 10:1 to 1:10 and wherein the coated metal oxide is selected from the group consisting of a coated titanium dioxide, coated zinc oxide, and mixtures of coated titanium dioxide and coated zinc oxide.

2. The agrochemical formulation of claim 1, wherein the photoprotective filter can not be detected visually.

3. The agrochemical formulation of claim 1, wherein the pesticide is dissolved or emulsified as droplets.

4. The agrochemical formulation of claim 1, wherein the coating comprises a silicon containing polymer and/or an inorganic oxide.

5. The agrochemical formulation of claim 1, wherein the organic UV photoprotective filter comprises 3-benzylidenecamphor and derivatives thereof, 4-aminobenzoic acid derivatives, esters of cinnamic acid, esters of salicylic acid, derivatives of benzophenone, esters of benzalmalonic acid, triazine derivatives, propane-1,3-diones, 2-phenylbenzimidazole-5-sulfonic acid and salts thereof; sulfonic acid derivatives of benzophenones, sulfonic acid derivatives of 3-benzylidenecamphor, 2-methyl-5-(2-oxo-3-bornylidene) sulfonic acid and salts thereof, derivatives of benzoylmethane, or aminohydroxy-substituted derivatives of benzophenones.

6. The agrochemical formulation of claim 1, wherein the weight ratio of the pesticide to the total mass of the organic UV photoprotective filter and the metal oxide is in the range of 50:1 to 1:10.

7. The agrochemical formulation of claim 1, wherein the pesticide is sensitive to UV-light.

8. The agrochemical formulation of claim 1, wherein the metal oxide comprises less than 0.05 mol % dopant.

9. A method for preparing the composition of claim 1, wherein a pesticide, an organic UV-filter and a coated metal oxide nanoparticle are mixed.

10. A method of combating harmful insects and/or phytopathogenic fungi, which comprises contacting plants, soil or habitat of plants in or on which the harmful insects and/or phytopathogenic fungi are growing or may grow, plants, or soil to be protected from attack or infestation by said harmful insects and/or phytopathogenic fungi with an effective amount of the agrochemical formulation of claim 1.

11. A method of controlling undesired vegetation, which comprises allowing a herbicidally effective amount of the agrochemical formulation of claim 1 to act on plants or their habitat.

12. A kit of parts, comprising as separate components

A) a composition comprising an organic UV photoprotective filter and a coated metal oxide nanoparticle, where the weight ratio of the organic UV photoprotective filter to the metal oxide is in a range of 10:1 to 1:10 and wherein the coated metal oxide is selected from the group consisting of a coated titanium dioxide, coated zinc oxide, and mixtures of coated titanium dioxide and coated zinc oxide, and B) a pesticide for combined application in a method of combating undesired vegetation, harmful insects and/or phytopathogenic fungi.

* * * * *